(12) United States Patent
Barnett et al.

(10) Patent No.: US 12,280,110 B2
(45) Date of Patent: Apr. 22, 2025

(54) METHOD FOR THE TREATMENT OR PREVENTION OF INFECTION-RELATED IMMUNE CONDITIONS USING A COMPOSITION COMPRISING IgM

(71) Applicants: Thomas Barnett, Chapel Hill, NC (US); David A. Ross, Cary, NC (US)

(72) Inventors: Thomas Barnett, Chapel Hill, NC (US); David A. Ross, Cary, NC (US)

(73) Assignee: Grifols Worldwide Operations Limited, Dublin (IE)

( * ) Notice: Subject to any disclaimer, the term of this patent is extended or adjusted under 35 U.S.C. 154(b) by 0 days.

(21) Appl. No.: 17/889,875

(22) Filed: Aug. 17, 2022

(65) Prior Publication Data

US 2023/0077855 A1 Mar. 16, 2023

Related U.S. Application Data

(60) Continuation of application No. 16/849,083, filed on Apr. 15, 2020, now abandoned, which is a continuation of application No. 16/456,689, filed on Jun. 28, 2019, now Pat. No. 10,660,956, which is a continuation of application No. 15/883,486, filed on Jan. 30, 2018, now abandoned, which is a division of application No. 15/147,226, filed on May 5, 2016, now Pat. No. 9,913,903.

(60) Provisional application No. 62/201,917, filed on Aug. 6, 2015.

(51) Int. Cl.
*A61K 39/40* (2006.01)
*A01K 67/0275* (2024.01)
*C07K 16/00* (2006.01)
*C07K 16/12* (2006.01)

(52) U.S. Cl.
CPC .......... *A61K 39/40* (2013.01); *A01K 67/0275* (2013.01); *C07K 16/00* (2013.01); *C07K 16/1214* (2013.01); *C07K 16/1228* (2013.01); *C07K 16/1232* (2013.01); *C07K 16/1282* (2013.01); *C07K 2317/52* (2013.01); *C07K 2317/70* (2013.01); *C07K 2317/73* (2013.01); *C07K 2317/76* (2013.01)

(58) Field of Classification Search
CPC .................................................... A61K 39/40
See application file for complete search history.

(56) References Cited

U.S. PATENT DOCUMENTS

| | | | |
|---|---|---|---|
| 4,652,533 A * | 3/1987 | Jolley | G01N 33/585 422/534 |
| 4,714,681 A * | 12/1987 | Reading | C07K 16/468 435/948 |
| 4,918,163 A | 4/1990 | Young et al. | |
| 5,190,752 A | 3/1993 | Möller et al. | |
| 5,410,025 A | 4/1995 | Moller et al. | |
| 6,307,028 B1 | 10/2001 | Lebing et al. | |
| 7,794,721 B2 | 9/2010 | Simon | |
| 9,913,903 B2 | 3/2018 | Barnett et al. | |
| 2003/0185827 A1 | 10/2003 | Rodriguez et al. | |
| 2006/0233781 A1* | 10/2006 | Pedersen | C12N 9/2462 424/164.1 |
| 2008/0145370 A1 | 6/2008 | Simon et al. | |
| 2008/0317857 A1 | 12/2008 | Farina et al. | |
| 2009/0298789 A1* | 12/2009 | Dobson | A61P 9/00 514/626 |
| 2010/0297187 A1 | 11/2010 | Stoloff et al. | |
| 2010/0303897 A1* | 12/2010 | Jerecic | A61P 25/28 424/139.1 |
| 2011/0059085 A1 | 3/2011 | Kim | |
| 2018/0153991 A1 | 6/2018 | Barnett et al. | |

FOREIGN PATENT DOCUMENTS

| | | |
|---|---|---|
| CL | 2016001977 | 5/2016 |
| EP | 03030088 A2 | 2/1989 |
| EP | 0345543 B1 | 12/1989 |
| EP | 3150629 A2 | 4/2017 |
| RU | 2191031 C2 | 10/2002 |
| WO | 8602362 | 4/1986 |
| WO | 2009140236 A2 | 11/2009 |

OTHER PUBLICATIONS

Gautam et al (Biotechnology Advances vol. 29, pp. 840-849) (Year: 2011).*
Barratt-Due et al., Polyvalent Immunoglobulin Significantly Attenuated the Formation of IL-1 (beta) in *Escherichia coli*-Induced Sepsis in Pigs, Immunobiology, 2012, pp. 683-689, vol. 218, No. 5.
Cesena, et al., Immune-modulation by polycylonal IgM treatment reduces atherosclerosis in hypercholesterolemic apoE-/-mice, Atherosclerosis, 220, pp. 59-65, 2012.
Hurez, et al., Pooled Normal Human Polyspecific IgM Contains Neutralizing Anti-Idiotypes to IgG Autoantibodies of Autoimmune Patents and Protects from Experimental Autoimmune Disease, Blood, vol. 90, No. 10, 1997, pp. 4004-4013.
Kreymann et al., Use of polyclonal immunoglobulins as adjunctive therapy for sepsis or septic shock, Critical Care Medicine, 2007, vol. 35, No. 12, pp. 2677-2685.
Linevsky et al., IL-8 release and neutrophil activation by Clostridium difficile toxin-exposed human monocytes, Am. J. Physiol. Gastrointest. Liver Physiol., 273: G1333-G1340, 1997.
Massironi et al., Minimal Concentration of Human IgM and IgG Antibodies Necessary to Protect Mice from Challenges with Live O6 *Escherichia coli*, FEMS Immunology and Medical Microbiology, 2011, pp. 193-201, vol. 63, No. 2.
Oesser et al., Protective capacity of a IgM/IgA-enriched polyclonal immunoglobulin-G preparation in endotoxemia, Res. Exp. Med., vol. 198, pp. 325-339, 1999.
Rossmann et al., In Vitro and In Vivo Activity of Hyperimmune Globulin Preparations Against Multiresistant Nosocomial Pathogens, Infection, 2014, pp. 169-175, vol. 43, No. 2.

(Continued)

*Primary Examiner* — Albert M Navarro
(74) *Attorney, Agent, or Firm* — Dinsmore & Shohl LLP

(57) ABSTRACT

Embodiments of the present invention provide methods for the treatment or prevention of infection-related immune conditions using compositions comprising IgM.

14 Claims, 5 Drawing Sheets

(56) References Cited

OTHER PUBLICATIONS

Sun et al., Essential role of the glucosyltransferase activity in Clostridium difficile toxin-induced secretion of TNF-a by macrophages, Microbial Pathogenesis, 16:298-305, 2009.
Tatum, Large scale recovery of biologically active IgM (95% pure) from human plasma obtained by therapeutic plasmapheresis, Journal of Immunological Methods, vol. 158, pp. 1-4, 1993.
Tramont et al., Progress in the development of an HIV vaccine, Expert Opinion on Emerging Drugs, vol. 8, No. 1, pp. 37-45, 2003.
Wand et al., IgM-Enriched Immunoglobulin Attenuates Systemic Endotoxin Activity in early Severe Sepsis: A Before-After Cohort Study, PLOS One, 2016, pp. 1-13, vol. 11, No. 8.
Norby-Teglund et al, Intravenous Polyclonal IgM-Enriched immunoglobulin Therapy in Sepsis: A Review of Clinical Efficacy in Relation to Microbiological Aetiology and Severity of Sepsis, Journal of Internal Medicine, 2006, pp. 509-516; vol. 260, No. 6.
Mahassni et al., Purification of a Murine IgM Monoclonal Antibody, Hybridoma, vol. 28, No. 3, 2009, pp. 189-197.
Gagnon et al., Purification of IgM Monoclonal Antibodies, BioPharma, 2008, pp. 1-10.
Extended European Search Report, dated Mar. 17, 2017, in European Patent Application No. 16179975.4, 11 pages.
Chilean Office Action, dated Jan. 17, 2018, in corresponding Chilean Patent Application No. 2016-0176.
Kamran Mousavi Hosseine, et al., Preparation of Enriched Immunoglobulin M and Immunoglobulin A from Human Plasma, Medical Journal of Islamic Republic of Iran, vol. 17, No. 4, Winter 1382, Feb. 2004, pp. 315-318.
Sharad P. Adekar et al;, A Natural Human IgM Antibody that Neutralizes Botulinum Neurotoxin in vivo, Hybridoma, vol. 27, No. 2, Apr. 1, 2008, pp. 65-69.
European Patent Office Search Report mailed Jan. 13, 2017 in reference to co-pending European Patent Application No. 16180425.7.
Nair et al., Impact of *Staphylococcus aureus* on Pathogenesis in Polymicrobial Infections, Infection and Immunity 82(6) pp. 2162-2169, 2014.
Norrby-Teglund et al., Relative Neutralizing Activity in Polyspecfic IgM, IgA and IgG Preparations against Group A Streptococcal Superantigens; Clinical Infectious Diseases, pp. 1175-1182, 2000.
Adekar et al., A Natural Human IgM Antibody that Neutralizes Botulinum Neurotoxin in vivo; Hybridoma 27(2) pp. 65-69, 2008.
European Office Action, dated Apr. 19, 2018, in corresponding European Patent Application No. 16179975.4 (33 pages).
Chilean Search Report, in corresponding Chilean Patent Application No. 2016-001977 (7 pages).
A. Marcuzzi et al, "Effects of anti-IgM suppression on polyclonally activated murine B cells: analysis of immunoglobulin mRNA, gene specific nuclear factors and cell cycle distribution", Nucleic Acids Research, Dec. 25, 1989, vol. 17, No. 24.
M. P. Horn et al: "Preclinical In Vitro and In Vitro Characterization of the Fully Human Monoclonal IgM Antibody KBPA101 Specific for Pseudomonas aeruginosa Serotype IATS-O11", Antimicrobial Agents and Chemotherapy, vol. 54, No. 6, Mar. 22, 2010, pp. 2338-2344).
C. Weyand et al: "Administration in vivo of recombinant interleukin 2 protects mice against septic death.", Journal of Clinical Investigation, vol. 79, No. 6, Jun. 1, 1987, pp. 1756-1763.
A.J. Walpen, et al., "Immunoglobulin M-enriched intravenous immunoglobulin inhibits classical pathway complement activation, but not bactericidal activity of human serum." Xenotransplantation, 2004, vol. 11, Issue 2, pp. 141-148, DOI: 10. 1046/j. 1399-3089. 2003. 00098.
M. Trautmann, et al., "Bacterial lipopolysaccharide (LPS)-specific antibodies in commercial human immunoglobulin preparations: superior antibody content of an Ig-M enriched product." Clinical & Experimental Immunology, Jan. 1998, vol. 111, Issue 1, pp. 81-90, DOI: 10. 1046/j. 1365-2249. 1998.
S. Takasu et al; Today's Therapy; 2002; pp. 149-150; vol. 44.
Patrone et al: TNF-Independent IL-8 Expression: Alterations in Bacteria Challenge Dose Cause Differential Human Monocytic Cytokine Response, J Immunol 2006; 177:1314-1322.
Pomorska-Mol et al (Journal of Immunology Research vol. 2020, Article ID 2614317, pp. 1-7) (Year: 2020).

\* cited by examiner

METHOD FOR THE TREATMENT OR PREVENTION OF INFECTION-RELATED IMMUNE CONDITIONS USING A COMPOSITION COMPRISING IgM

CROSS REFERENCE TO RELATED APPLICATIONS

This application is a continuation of U.S. patent application Ser. No. 16/849,083, filed Apr. 15, 2020, which is a continuation of U.S. patent application Ser. No. 16/456,689, now U.S. Pat. No. 10,660,956, filed Jun. 28, 2019, which is a division of U.S. patent application Ser. No. 15/147,226, filed May 5, 2016, which claims priority to U.S. Provisional Patent Application No. 62/201,917, filed Aug. 6, 2015, the contents of all of which are specifically incorporated herein by reference.

FIELD OF THE INVENTION

The present invention relates to the treatment or prevention of immune symptoms or conditions by administering compositions comprising IgM.

BACKGROUND OF THE INVENTION

Microbial species can become highly deleterious to the infected patient, if that individual cannot clear the infection. Infections can also become septic, spreading from an infected organ into the blood stream. These septic infections have a poor outcome for patients.

It is well characterized that plasma-derived IgM can bind to and prevent endotoxin-mediated toxicity towards a patient. This is attributed to the inherent ability or preference of IgM to bind glycans thereby preventing their effects. These toxic effects of endotoxins are typically in response to bacterial death or lysis induced by antibiotics or the immune system of the patient.

In addition, the use of IgM compositions or IgM enriched compositions has been proposed for the treatment of autoimmune diseases or atherosclerosis based on the interaction of IgM with specific hallmarks of said diseases, for example, autoantibodies (Hurez, V. et. al. "Pooled Normal Human Polyspecific IgM Contains Neutralizing Anti-Idioitypes to IgG Autoantibodies of Autoimmune Patients and Protects from Exaperimental Autoimmune Disease", Blood, 1997, Vol. 90, No. 10, 4004-4013; and Cesena, H Y. "Immunemodulation by polyclonal IgM treatment reduces atherosclerosis in hypercholesterolemic apoE−/−mice", Atherosclerosis, 2012, Vol. 220, 59-65).

Septic conditions and other complications of microbial infections are often associated with an over-stimulation of the immune system, and are often impossible to control due to their exaggerated magnitude and quick evolution. Therefore, there remains a need for effective treatment regimens to reduce, inhibit or prevent over-stimulation of the immune system.

SUMMARY OF THE INVENTION

An embodiment of the present invention provides a composition comprising, consisting essentially of, or consisting of plasma-derived IgM and optionally one or more excipients in a pharmaceutical carrier.

In a further embodiment, the present invention provides a composition comprising IgM for use in the treatment of sepsis.

In a further embodiment, the present invention provides a composition comprising IgM for use in the treatment of immune complications produced by infections.

In a further embodiment, the present invention provides a method for the treatment of immune complications produced by infections in patients in need thereof, characterized in that it comprises the administration of a composition comprising IgM.

In a further embodiment, the present invention also provides a method for the immunomodulation of an infection in a patient in need thereof, characterized in that it comprises the administration of a composition comprising IgM.

BRIEF DESCRIPTION OF THE FIGURES

For a better understanding, the present invention is described in more detail below with reference to the accompanying figures, which are presented by way of example, and with reference to illustrative examples which are not a limitation of the present invention.

In FIG. 4A, the y-axis shows the fold increase in NF-κB activity, as measured by the NF-κB SEAP reporter, which is proportional to the induction of NF-κB activity; and the x-axis shows the various treatment groups. In FIG. 4B the y-axis shows the concentration of IL-8 secreted into the culture supernatant; and the x-axis shows the various treatment groups. In FIG. 4B "UD" indicates that the IL-8 was undetectable in the untreated control group. In both figures, standard error is indicated on each bar.

DETAILED DESCRIPTION OF THE INVENTION

Figure 1:
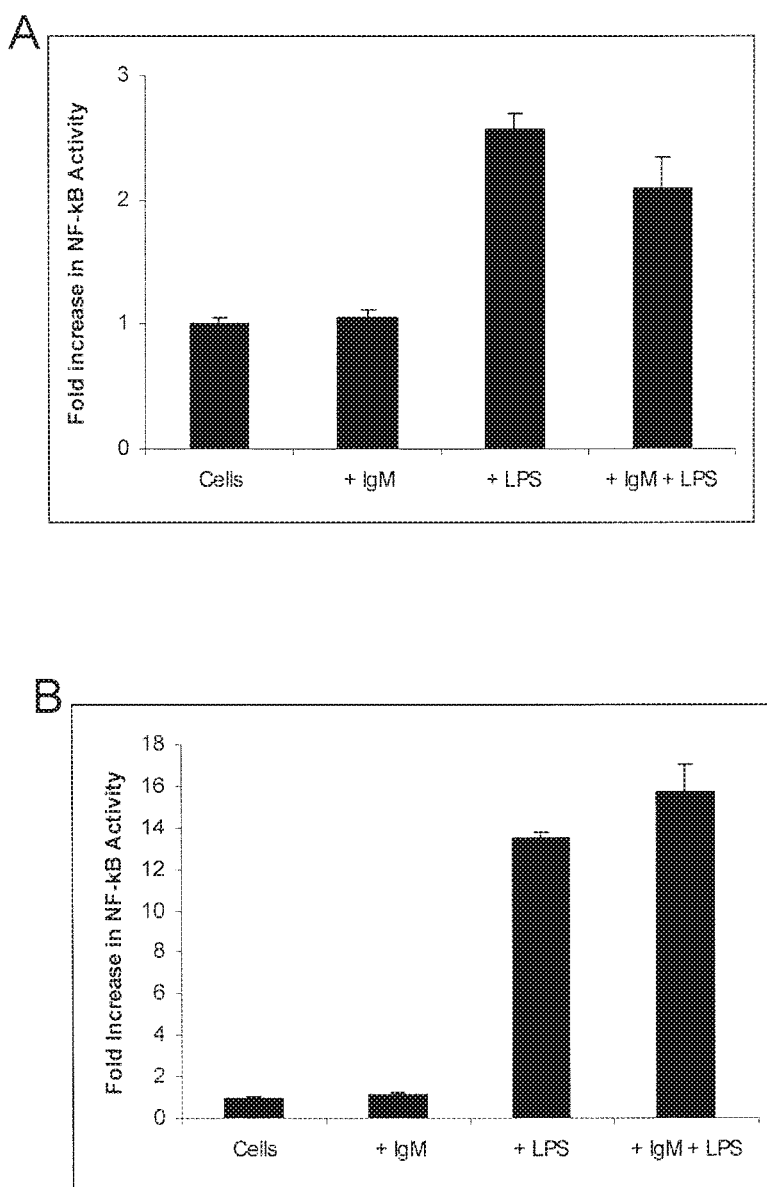
FIG. 1 shows the results obtained for the assessment of the effect of IgM on *Escherichia coli* LPS-induced NF-κB activation in THP-1 cells harboring a stable NF-κB reporter plasmid. Both in FIGS. 1A and 1B, the y-axis shows the fold increase in NF-κB activity, as measured by the NF-κB SEAP reporter, said increase is proportional to the induction of NF-κB activity. Also in both FIGS. 1A and 1B), the various treatment groups are shown on the x-axis. Standard error is indicated on each bar.

The present inventors, after exhaustive and extensive experimentation and investigation, have found that IgM compositions exhibit immunomodulatory activities (for example, by decreasing NF-κB activity induction and/or reducing proliferation of peripheral blood mononuclear cells) which make said compositions suitable for the treatment of conditions related to over-stimulation of the immune system, for example, over-stimulation of the immune-system associated with septic conditions.

An embodiment of the present invention provides a composition comprising, consisting essentially of, or consisting of plasma-derived IgM and optionally one or more excipients in a pharmaceutical carrier. According to particular embodiments, the one or more excipients and/or the pharmaceutical carrier are synthetic, i.e., non-naturally occurring.

As used herein, the term "pharmaceutically acceptable carrier" refers to a diluent, adjuvant, excipient, or vehicle with which plasma-derived IgM of the present invention is administered. Such carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Saline solutions and aqueous dextrose and glycerol solutions can also be employed as liquid carriers, particularly for injectable solutions. According to particular embodiments, the pharmaceutically acceptable carrier is synthetic (i.e., the carrier is not naturally-occurring).

Non-limiting examples of suitable excipients include starch, glucose, lactose, sucrose, gelatin, silica gel, sodium stearate, glycerol monostearate, talc, sodium chloride, glycerol, propylene glycol, water, ethanol and the like. Excipients may also include wetting or emulsifying agents, or pH buffering agents such as acetates, citrates or phosphates; antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose. According to particular embodiments, the one or more excipients are synthetic (i.e., the excipients are not naturally-occurring).

Embodiments of the present invention also relate to methods for immunomodulating the responses to microbial infections, independent of endotoxin-mediated immune response.

Therefore, in a first embodiment, the present invention provides a composition comprising IgM for use in the treatment of sepsis.

In a second embodiment, the present invention provides a composition comprising IgM for use in the treatment of immune complications produced by infections.

In a further embodiment, the present invention provides a method for the treatment of immune complications produced by infections in patients in need thereof, characterized in that it comprises the administration of a composition comprising IgM.

Moreover, the present invention also provides a method for the immunomodulation of an infection in a patient in need thereof, characterized in that it comprises the administration of a composition comprising IgM.

As used herein, "hypercytokinemia" and its plural mean an immune complication charactirez by an excess of pro-inflammatory cytokine production as a result of a positive feedback loop between cytokines and white blood cells, including T-cells and macrophages.

As used herein, "hypercoagulopathy" and its plural mean an immune complication resulting from extreme activation of certain blood cell components, like platelets, and blood coagulation factors of the extrinsic and intrinsic pathways by microbes and their products.

In one embodiment, the present invention provides a composition comprising IgM for use in the treatment of sepsis. According to particular embodiments, the composition comprises, consists essentially of, or consists of plasma-derived IgM and optionally one or more excipients in a pharmaceutical carrier.

Sepsis can be produced by one or more bacteria (gram-positive or gram-negative), one or more fungi (for example, *Aspergillus flavus*), one or more virus or combinations thereof. In a preferred embodiment, sepsis is produced by one or more bacteria, more preferably sepsis is produced by *Escherichia coli, Pseudomonas aeruginosa, Staphyloccus aureus, Klebsiella pneumoniae, Streptococcus pneumoniae, Clostridium difficile, Clostridium botulinum*, or combinations thereof.

The treatment of sepsis or the septic condition is performed through the treatment of immune complications, such as pro-inflammatory responses or hyperactivation of the is immune system, which in turn is performed through immunomodulation. Said immunomodulation is preferably independent of endotoxin-mediated immune response and can be exerted through various means. In a preferred embodiment, the immunomodulation is performed through inhibition NF-κB induction. In another embodiment, immunomodulation is performed through the inhibition of proliferation of peripheral blood mononuclear cells, preferably T-cells. In the most preferred embodiment, immunomodulation is exerted through both means mentioned above.

Preferably, the composition has at least 90% (w/v) of IgM purity, more preferably at least 95% of IgM purity. In the most preferred embodiment, the composition has a 95% (w/v) of IgM purity.

The dose to be administered of the composition is preferably from 75 mg IgM/kg patient to 1 g IgM/kg patient, more preferably from 75 mg IgM/kg patient to 600 g IgM/kg patient and, most preferably, from 75 mg IgM/kg patient to 300 g IgM/kg patient. In addition, the composition is preferably provided or administered at least once a week or every other day or thrice weekly or on a daily basis.

In addition, said IgM can be recombinant, plasma-derived, cell culture-derived, transgenic or chemically synthesized.

If the IgM is recombinant, it can be obtained according to any technique known in the field of expression, production and purification of proteins. For example, IgM nucleic acid sequence can be inserted in any vector suitable for expression in the elected host cell, e.g. bacteria (*Escherichia coli, Bacillus subtilis, Salmonella typhimurium, Pseudomonas, Streptomyces* and *Staphylococcus*), yeast (*Saccharomyces, Pichia* or *Kuyveromyces* to genus), insect cells (*Bombyx mori, Mamestra brassicae, Spodoptera frugiperda, Trichoplusia ni* or *Drosophila melanogaster*) or mammalian cells (HeLa cells, baby hamster kidney (BHK) cells, monkey kidney cells (COS-1), human hepatocellular carcinoma cells (e.g., Hep G2), human adenovirus transformed 293 cells, mouse L-929 cells, HaK hamster cell lines, murine 3T3 cells derived from Swiss, Balb-c or NIH mice, CV-1 cell line, cell strains derived from in vitro culture of primary tissue or primary explants.

Cell culture-derived IgM can be produced through any method or procedure known in the state of the art, for example, the hybridoma method.

Transgenic and chemically synthesized IgM can be produced through any method or procedure known in the state of the art.

In a preferred embodiment, IgM is plasma-derived IgM, isolated from a suitable fraction of plasma, for example, the wash of the two ANX columns procedures after collecting IgG, as described in U.S. Pat. No. 6,307,028 or further purifying said fraction by negative selection affinity chromatography or size exclusion chromatography.

Regarding said plasma-derived IgM, it can, optionally, be isolated or purified to increase the relative amounts of specific antibodies against a given exotoxin, secreted protein, microbial species or combinations thereof.

According to particular embodiments, it is contemplated that the composition comprising IgM is administered alone.

In another embodiment, the composition comprising IgM is administered together with one or more other compositions or molecules. Said other compositions or molecules are preferably selected from anti-inflammatory molecules, antibiotics (for example, small molecule antibiotics, molecules that are antimicrobial in nature, natural or synthetic peptide antimicrobials and/or proteins with antimicrobial properties), other immunomodulators or combinations thereof. In a preferred embodiment, said other compositions or molecules are vancomycin, meropenem, lactoferrin or combinations thereof. The administration of the composition comprising IgM together with one or more other compositions or molecules as mentioned above includes the administration at the same time of all the compositions or molecules or the administration one after the other of the compositions or molecules to be provided.

The composition comprising IgM can be used both, for the treatment of sepsis, as mentioned above, and for the prevention of said disease.

In a further embodiment, the present invention discloses a composition comprising IgM for use in the treatment of immune complications produced by an infection.

Infection can be produced by one or more bacteria (grampositive or gram-negative), one or more fungi (for example, *Aspergillus flavus*), one or more virus or combinations thereof. In a preferred embodiment, the infection is produced by one or more bacteria, more preferably the infection is produced by *Escherichia coli, Pseudomonas aeruginosa, Staphyloccus aureus, Klebsiella pneumoniae, Streptococcus pneumoniae, Clostridium difficile, Clostridium botulinum* or combinations thereof.

The treatment of immune complications, such as proinflammatory responses or hyperactivation of the immune system, is performed through immunomodulation. Said immunomodulation is preferably independent of endotoxin-mediated immune response and can be exerted through various means. In a preferred embodiment, the immunomodulation is performed through inhibition NF-κB induction. In another embodiment, immunomodulation is performed through the inhibition of proliferation of peripheral blood mononuclear cells, preferably T-cells. In the most preferred embodiment, immunomodulation is exerted through both means mentioned above.

The composition preferably has at least 90% (w/v) of IgM purity, more preferably at least to 95% (w/v) of IgM purity.

In the most preferred embodiment, the composition used comprises 95% (w/v) of IgM purity.

The dose to be administered of the composition is preferably from 75 mg IgM/kg patient to 1 g IgM/kg patient, more preferably from 75 mg IgM/kg patient to 600 g IgM/kg patient and, most preferably, from 75 mg IgM/kg patient to 300 g IgM/kg patient. In addition, the composition is preferably provided or administered at least once a week or every other day or thrice weekly or on a daily basis.

In addition, said IgM can be recombinant, plasma-derived, cell culture-derived, transgenic or chemically synthesized.

If the IgM is recombinant, it can be obtained according to any technique known in the field of expression, production and purification of proteins. For example, IgM nucleic acid sequence can be inserted in any vector suitable for expression in the elected host cell, e.g. bacteria (*Escherichia coli, Bacilus subtilis, Salmonella typhimurium, Pseudomonas, Streptomyces* and *Staphylococcus*), yeast (*Saccharomyces, Pichia* or *Kuyveromyces* genus), insect cells (*Bombyx mori, Mamestra brassicae, Spodoptera frugiperda, Trichoplusia ni* or *Drosophila melanogaster*) or mammalian cells (HeLa cells, baby hamster kidney (BHK) cells, monkey kidney cells (COS-1), human hepatocellular carcinoma cells (e.g., Hep G2), human adenovirus transformed 293 cells, mouse L-929 cells, HaK hamster cell lines, murine 3T3 cells derived from Swiss, Balb-c or NIH mice, CV-1 cell line, cell strains derived from in vitro culture of primary tissue or primary explants.

Cell culture-derived IgM can be produced through any method or procedure known in the state of the art, for example, the hybridoma method.

Transgenic and chemically synthesized IgM can be produced through any method or procedure known in the state of the art.

In a preferred embodiment, IgM is plasma-derived IgM, isolated from a suitable fraction of plasma, for example, the wash of the two ANX columns procedures after collecting IgG, as to described in U.S. Pat. No. 6,307,028 or further purifying said fraction by negative selection affinity chromatography or size exclusion chromatography.

In another preferred embodiment, the immune complication produced by an infection is hypercytokinemia, hypercoagulopathy or organ failure.

Regarding said plasma-derived IgM, it can, optionally, be isolated or purified to increase the relative amounts of specific antibodies against a given exotoxin, secreted protein, microbial species or combinations thereof.

According to particular embodiments, it is contemplated that the composition comprising IgM is administered alone.

In another embodiment, the composition comprising IgM is administered together with one or more other compositions or molecules. Said other compositions or molecules are preferably selected from anti-inflammatory molecules, antibiotics (for example, small molecule antibiotics, molecules that are antimicrobial in nature, natural or synthetic peptide antimicrobials and/or proteins with antimicrobial properties), other immunomodulators or combinations thereof. In a preferred embodiment, said other compositions or molecules are vancomycin, meropenem, lactoferrin or combinations thereof. The administration of the composition comprising IgM together with one or more other compositions or molecules as mentioned above includes the administration at the same time of all the compositions or molecules or the administration one after the other of the compositions or molecules to be provided.

The composition comprising IgM can be used both, for the treatment of the immune complications produced by an infection, as mentioned above, and for the prevention of said immune complications.

In an additional embodiment, the present invention refers to a method for the treatment of immune complications produced by infections in patients in need thereof, characterized in that it comprises the administration of a composition comprising IgM.

The infection can be produced by one or more bacteria (gram-positive or gram-negative), one or more fungi (for example, *Aspergillus flavus*), one or more virus or combinations thereof. In a preferred embodiment, the infection is produced by one or more bacteria, more preferably the infection is produced by *Escherichia coli, Pseudomonas aeruginosa, Staphyloccus aureus, Klebsiella pneumoniae, Streptococcus pneumoniae, Clostridium difficile, Clostridium botulinum* or combinations thereof.

The treatment of immune complications, such as pro-inflammatory responses or hyperactivation of the immune system, is performed through immunomodulation. Said immunomodulation is preferably independent of endotoxin-mediated immune response and can be exerted through various means. In a preferred embodiment, the immunomodulation is performed through inhibition NF-κB induction. In another embodiment, immunomodulation is performed through the inhibition of proliferation of peripheral blood mononuclear cells, preferably T-cells. In the most preferred embodiment, immunomodulation is exerted through both means mentioned above.

The composition preferably has at least 90% (w/v) of IgM purity, more preferably at least 95% (w/v) of IgM purity. In the most preferred embodiment, the composition used comprises 95% (w/v) of IgM purity.

The dose to be administered of the composition is preferably from 75 mg IgM/kg patient to 1 g IgM/kg patient, more preferably from 75 mg IgM/kg patient to 600 g IgM/kg patient and, most preferably, from 75 mg IgM/kg patient to 300 g IgM/kg patient. In addition, the composition is preferably provided or administered at least once a week or every other day or thrice weekly or on a daily basis.

In addition, said IgM can be recombinant, plasma-derived, cell culture-derived, transgenic or chemically synthesized.

If the IgM is recombinant, it can be obtained according to any technique known in the field of expression, production and purification of proteins. For example, IgM nucleic acid sequence can be inserted in any vector suitable for expression in the elected host cell, e.g. bacteria (*Escherichia coli, Bacilus subtilis, Salmonella typhimurium, Pseudomonas, Streptomyces* and *Staphylococcus*), yeast (*Saccharomyces, Pichia* or *Kuyveromyces* genus), insect cells (*Bombyx mori, Mamestra brassicae, Spodoptera frugiperda, Trichoplusia ni* or *Drosophila melanogaster*) or mammalian cells (HeLa cells, baby hamster kidney (BHK) cells, monkey kidney cells (COS-1), human hepatocellular carcinoma cells (e.g., Hep G2), human adenovirus transformed 293 cells, mouse L-929 cells, HaK hamster cell lines, murine 3T3 cells derived from Swiss, Balb-c or NIH mice, CV-1 cell line, cell strains derived from in vitro culture of primary tissue or primary explants.

Cell culture-derived IgM can be produced through any method or procedure known in the state of the art, for example, the hybridoma method.

Transgenic and chemically synthesized IgM can be produced through any method or procedure known in the state of the art.

In a preferred embodiment, IgM is plasma-derived IgM, isolated from a suitable fraction of plasma, for example, the wash of the two ANX columns procedures after collecting IgG, as described in U.S. Pat. No. 6,307,028 or further purifying said fraction by negative selection affinity chromatography or size exclusion chromatography.

Regarding said plasma-derived IgM, it can, optionally, be isolated or purified to increase the relative amounts of specific antibodies against a given exotoxin, secreted protein, microbial species or combinations thereof.

According to particular embodiments, it is contemplated that the composition comprising IgM is administered alone.

In another embodiment, the composition comprising IgM is administered together with one or more other compositions or molecules. Said other compositions or molecules are preferably selected from anti-inflammatory molecules, antibiotics (for example, small molecule antibiotics, molecules that are antimicrobial in nature, natural or synthetic peptide antimicrobials and/or proteins with antimicrobial properties), other immunomodulators or combinations thereof. In a preferred embodiment, said other compositions or molecules are vancomycin, meropenem, lactoferrin or combinations thereof. The administration of the composition comprising IgM together with one or more other compositions or molecules as mentioned above includes the administration at the same time of all the compositions or molecules or the administration one after the other of the compositions or molecules to be provided.

The method of the present invention can be used both, for the treatment of immune complications produced by an infection, as mentioned above, and for the prevention of said immune complications.

Finally, the present invention also discloses a method for the immunomodulation of an infections in a patient in need thereof, characterized in that it comprises the administration of a composition comprising IgM.

Said immunomodulation can be used for the treatment or the prevention of infections or infection-related symptoms or conditions.

The infection can be produced by one or more bacteria (gram-positive or gram-negative), one or more fungi (for example, *Aspergillus flavus*), one or more virus or combinations thereof. In a preferred embodiment, the infection is produced by one or more bacteria, more preferably the infection is produced by *Escherichia coli, Pseudomonas aeruginosa, Staphyloccus aureus, Klebsiella pneumoniae, Streptococcus pneumoniae, Clostridium difficile, Clostridium botulinum* or combinations thereof.

Said immunomodulation allows the treatment of immune complications, such as pro-inflammatory responses or hyperactivation of the immune system and is preferably independent of endotoxin-mediated immune response and can be exerted through various means. In a preferred embodiment, the immunomodulation is performed through inhibition NF-κB induction. In another embodiment, immunomodulation is performed through the to inhibition of proliferation of peripheral blood mononuclear cells, preferably T-cells. In the most preferred embodiment, immunomodulation is exerted through both means mentioned above.

The composition preferably has at least 90% (w/v) of IgM purity, more preferably at least 95% (w/v) of IgM purity. In the most preferred embodiment, the composition used comprises 95% (w/v) of IgM purity.

The dose to be administered of the composition is preferably from 75 mg IgM/kg patient to 1 g IgM/kg patient, more preferably from 75 mg IgM/kg patient to 600 g IgM/kg patient and, most preferably, from 75 mg IgM/kg patient to 300 g IgM/kg patient. In addition, the composition is preferably provided or administered at least once a week or every other day or thrice weekly or on a daily basis.

In addition, said IgM can be recombinant, plasma-derived, cell culture-derived, transgenic or chemically synthesized.

If the IgM is recombinant, it can be obtained according to any technique known in the field of expression, production and purification of proteins. For example, IgM nucleic acid sequence can be inserted in any vector suitable for expression in the elected host cell, e.g. bacteria (*Escherichia coli, Bacilus subtilis, Salmonella typhimurium, Pseudomonas, Streptomyces* and *Staphylococcus*), yeast (*Saccharomyces, Pichia* or *Kuyveromyces* genus), insect cells (*Bombyx mori, Mamestra brassicae, Spodoptera frugiperda, Trichoplusia ni* or *Drosophila melanogaster*) or mammalian cells (HeLa cells, baby hamster kidney (BHK) cells, monkey kidney cells (COS-1), human hepatocellular carcinoma cells (e.g., Hep G2), human adenovirus transformed 293 cells, mouse L-929 cells, HaK hamster cell lines, murine 3T3 cells derived from Swiss, Balb-c or NIH mice, CV-1 cell line, cell strains derived from in vitro culture of primary tissue or primary explants.

Cell culture-derived IgM can be produced through any method or procedure known in the state of the art, for example, the hybridoma method.

Transgenic and chemically synthesized IgM can be produced through any method or procedure known in the state of the art.

In a preferred embodiment, IgM is plasma-derived IgM, isolated from a suitable fraction of plasma, for example, the wash of the two ANX columns procedures after collecting IgG, as described in U.S. Pat. No. 6,307,028 or further purifying said fraction by negative selection affinity chromatography or size exclusion chromatography.

Regarding said plasma-derived IgM, it can, optionally, be isolated or purified to increase the relative amounts of specific antibodies against a given exotoxin, secreted protein, microbial species or combinations thereof.

According to particular embodiments, it is contemplated that the composition comprising IgM is administered alone.

In another embodiment, the composition comprising IgM is administered together with one or more other compositions or molecules. Said other compositions or molecules are preferably selected from anti-inflammatory molecules, antibiotics (for example, small molecule antibiotics, molecules that are antimicrobial in nature, natural or synthetic peptide antimicrobials and/or proteins with antimicrobial properties), other immunomodulators or combinations thereof. In a preferred embodiment, said other compositions or molecules are vancomycin, meropenem, lactoferrin or combinations thereof. The administration of the composition comprising IgM together with one or more other compositions or molecules as mentioned above includes the administration at the same time of all the compositions or molecules or the administration one after the other of the compositions or molecules to be provided.

The embodiments described herein are intended to be exemplary of the invention and not limitations thereof. One skilled in the art will appreciate that modifications to the embodiments and examples of the present disclosure may be made without departing from the scope of the present disclosure.

The embodiments of the invention are described above using the term "comprising" and variations thereof. However, it is the intent of the inventors that the term "comprising" may be substituted in any of the embodiments described herein with "consisting of" and "consisting essentially of" without departing from the scope of the invention. Unless specified otherwise, all values provided herein include up to and including the starting points and end points given.

The following examples further illustrate embodiments of the invention and are to be construed as illustrative and not in limitation thereof.

EXAMPLES

Example 1. Analysis of the influence of IgM in NF-κB activity induction by *Escherichia coli*'s lipopolysaccharide (LPS) endotoxin.

Human THP-1 monocyte cell line harboring a stable plasmid with a NF-κB-dependent promoter driving a secreted alkaline phosphatase (SEAP) reporter (Invivogen, San Diego, CA USA), as a means of monitoring NF-κB signaling pathway activation, was used to carry out this experiment.

Cells were cultured in proliferation media according to manufacturer's recommendations.

The experiment was performed with both LPS derived from *Escherichia coli* strain O111:B4 and LPS derived from *Escherichia coli* strain K12. THP-1 cells mentioned above, were treated with 100 ng/mL of *Escherichia coli* LPS derived from strain O111:B4 (see FIG. 1A) or 1 ng/mL of *Escherichia coli* LPS derived from strain K12 (see FIG. 1B) for 24 hours.

When IgM was used, LPS was pre-incubated with purified IgM (purity of 95% (w/v) or higher) prior to treatment of cells.

For NF-κB activity assays, $1\times10^5$ cells were seeded in each well of a 96-well plate. Assay culture media was the same as proliferation media, except that it contained reduced serum to diminish the non-specific effects of fetal bovine serum (FBS)-derived proteins. Cells were treated as described above, using a final concentration of 2.5 mg/mL IgM (at least 95% (w/v) pure IgM).

NF-κB activity was determined by assessing the levels of Secreted Alkaline Phosphatase (SEAP) in the supernatant, as measured by the Quanti-Blue assay (Invivogen, San Diego, CA USA) and performed according to manufacturer's instructions. Relative cell number at the time of the NF-κB assay was determined by Cell Titer Glow (Promega Corp. Madison, WI, USA) and performed according to manufacturer's instructions. The relative NF-κB activity shown in FIG. 1 was calculated by normalizing the NF-κB assay values to the relative cell number as determined by Cell Titer Glow assay, then standardizing experimental controls to the value of 1.

Surprisingly, it was observed that purified IgM did not have any significant effect on LPS-mediated activation of NF-κB signaling in any of the cases tested and mentioned above (see FIG. 1A and FIG. 1B).

Example 2. Analysis of the influence of IgM in NF-κB activity induction by *Clostridium difficile*'s Toxoid B. *Clostridium difficile*'s toxins are know to induce cytokine secretion, including IL-8 and TNF-α, in monocytes (Linevsky, J K., et. al., "IL-8 release and neutrophil activation by *Clostridium difficile* toxin-exposed human monocytes, Am J Physiol Gastrointest Liver Physiol, 1997, 273, G1333-G1340; and Sun, X., et. al. "Essential role of the glucosyltransferase activity in *Clostridium difficile* toxin-induced secretion of TNF-α by macrophages", Microbial Pathogenesis, 2009, 16, 298-305). Each of these cytokines is also known to be induced upon activation of NF-κB.

Therefore, it was tested whether *Clostridium difficile*'s Toxoid B could induce NF-κB signaling in Human THP-1 cells harboring a stably integrated NF-κB reporter plasmid (Invivogen, San Diego, CA USA), as mentioned above. Cells were cultured in proliferation media according to manufacturer's recommendations.

Since the toxins themselves are cytotoxic, inactivated toxoids were used to avoid complicated interpretations of the results. For NF-κB activity assays, $2\times10^5$ cells were seeded in each well of a 96-well plate for 24 hours prior to treatments. Cells were then treated with several concentrations of *C. difficile*'s Toxoid A (List Biological Labs, Inc, Campbell, CA USA) or Toxoid B (List Biological Labs, Inc, Campbell, CA USA). NF-κB activity was determined by assessing the levels of Secreted Alkaline Phosphatase (SEAP) in the supernatant, as measured by the Quanti-Blue assay (Invivogen, San Diego, CA USA) and performed according to manufacturer's instructions. Relative cell number at the time of the NF-κB assay was determined by Cell Titer Glow (Promega Corp. Madison, WI, USA) and performed according to manufacturer's instructions. The relative NF-κB activity shown in FIG. 2 was calculated by normalizing the NF-κB assay values to the relative cell number as determined by Cell Titer Glow assay, then standardizing experimental controls to the value of 1.

Figure 2:
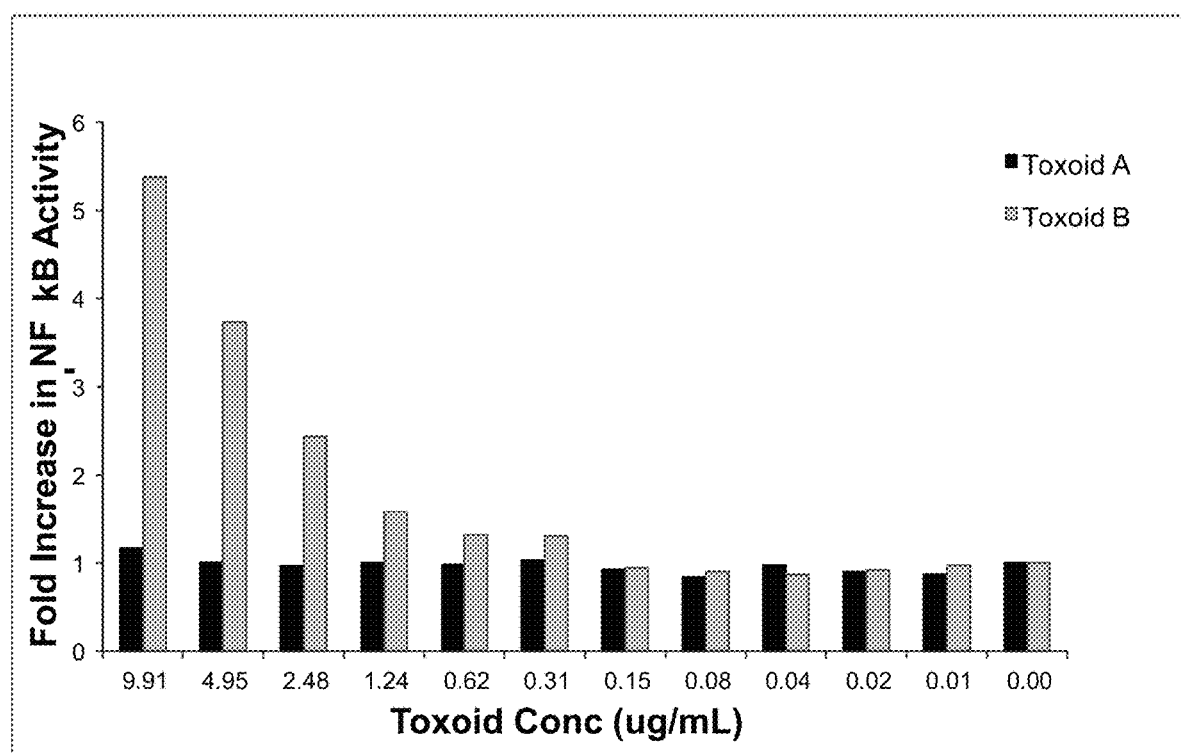
FIG. 2 shows the results obtained for the induction of NF-κB by Toxoid A or Toxoid B of *Clostridium difficile* in THP-1 cells harboring a stable NF-κB reporter plasmid. The fold increase in NF-κB activity, as measured by the NF-κB SEAP reporter, is indicated on the y-axis and is proportional to the induction of NF-κB activity. The concentration of Toxoid A or Toxoid B in µg/mL is shown in the x-axis.

While Toxoid A did not induce NF-κB signaling in these cells, Toxoid B showed induction of the NF-κB reporter in these cells (see FIG. 2).

The capacity of a solution of IgM (purity of 90-95% of IgM) to inhibit NF-κB activation was assessed, as compared to BSA (Bovine Serum Albumin) controls.

Cells were treated with 9.25 m/mL of *Clostridium difficile*'s Toxoid B for 24 hours. In case of treatment also with BSA or IgM composition, Toxoid B was pre-incubated with said BSA or with the solution of IgM (purity of 90-95% (w/v) of IgM) prior to treatment of cells.

Figure 3:
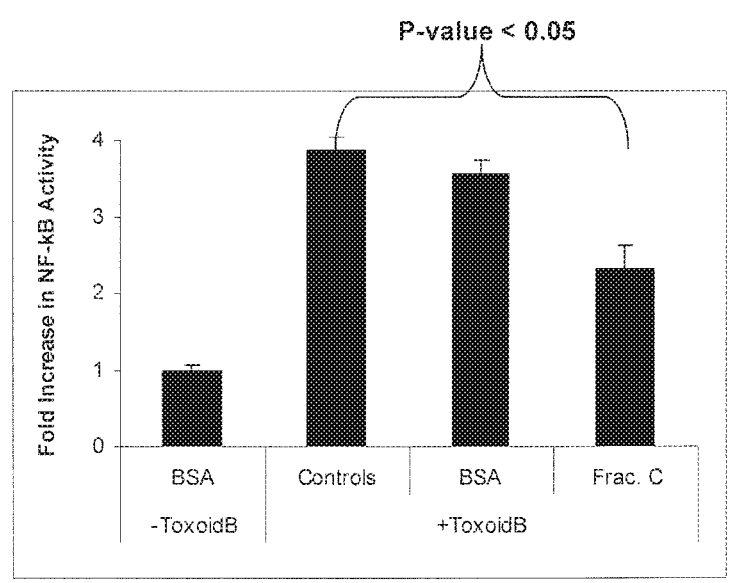
FIG. 3 shows the results obtained for the inhibition of *Clostridium difficile*'s Toxoid B-induced NF-κB activation in THP-1 cells harboring a stable NF-κB reporter plasmid. The fold increase in NF-κB activity, as measured by the NF-κB SEAP reporter, is indicated on the y-axis and is proportional to the induction of NF-κB activity. The various treatment groups are shown on the x-axis. Standard error is indicated on each bar.

Assay culture media was the same as proliferation media, except that it contained 0.025 μM Vitamin D3. For NF-κB activity assays, $2\times10^5$ cells were seeded in each well of a 96-well plate for 24 hours prior to treatments. Cells were then treated as described above, using a final concentration of 3 mg/mL IgM (90-95% (w/v) purity of IgM) or BSA. NF-κB activity was determined by assessing the levels of Secreted Alkaline Phosphatase (SEAP) in the supernatant, as measured by the Quanti-Blue assay (Invivogen, San Diego, CA USA) and performed according to manufacturer's instructions. Relative cell number at the time of the NF-κB assay was determined by Cell Titer Glow (Promega Corp. Madison, WI, USA) and performed according to manufacturer's instructions. The relative NF-κB activity shown in FIG. 3 was calculated by normalizing the NF-κB assay values to the relative cell number as determined by Cell Titer Glow assay, then standardizing experimental controls to the value of 1.

BSA had no effect on Toxoid B activation of NF-κB, whereas the solution of IgM mentioned above attenuated the Toxoid B effect (see FIG. 3).

Example 3. Analysis of the influence of IgM in NF-κB activity induction and IL-8 secretion by *Klebsiella pneumoniae* and *Pseudomonas aeruginosa*.

Since IgM was unable to attenuate the NF-κB signaling mediated by *E. coli*. cell wall endotoxin LPS (see example 1), the effect of purified IgM on intact whole bacteria (possessing cell wall components like LPS) was assessed.

Treatment with a live culture of microbes would have overtaken and hampered the results of a mammalian cell culture assay system. Therefore, whole bacteria (*Klebsiella pneumoniae* and *Pseudomonas aeruginosa*) were formaldehyde-fixed to kill said bacteria, while keeping the cells intact.

THP-1 cells harboring a stable NF-κB reporter plasmid as mentioned above were treated with formaldehyde killed *Klebsiella pneumoniae* and *Pseudomonas aeruginosa* for 24 hours.

When IgM was used, the above-mentioned microbes were co-treated with purified IgM at the time of treatment.

For NF-κB activity assays, $1\times10^5$ cells were seeded in each well of a 96 well plate. Assay culture media is the same as proliferation media, except that it contains reduced serum to diminish the non-specific effects of FBS-derived proteins. Cells were treated as described in the figure legend, using a final concentration of 2.5 mg/mL IgM (at least 95% pure IgM). NF-κB activity was determined by assessing the levels of Secreted Alkaline Phosphatase (SEAP) in the supernatant, as measured by the Quanti-Blue assay (Invivogen, San Diego, CA USA) and performed according to manufacturer's instructions. Relative cell number at the time of the NF-κB assay was determined by Cell Titer Glow (Promega Corp. Madison, WI, USA) and performed according to manufacturer's instructions. The relative NF-κB activity shown was calculated by normalizing the NF-κB assay values to the relative cell number as determined by Cell Titer Glow assay, then standardizing experimental controls to the value of 1.

Figure 4:
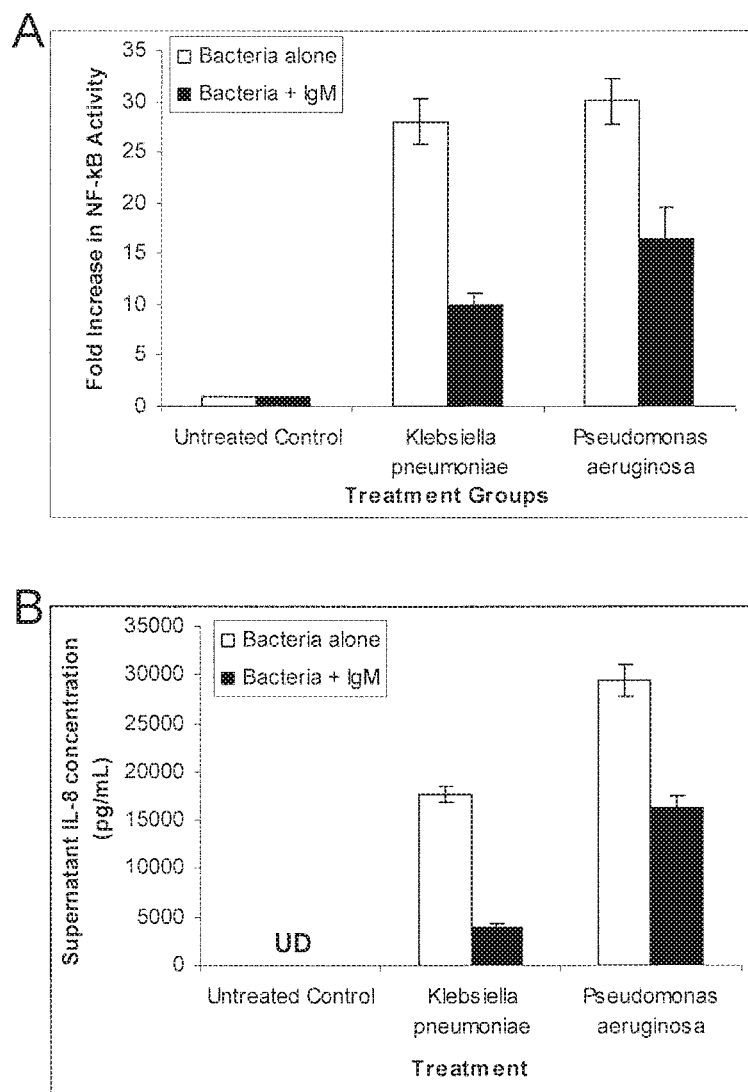
FIG. 4 shows the results for the inhibition of *Klebsiella pneumoniae* and *Pseudomonas aeruginosa*-induced NF-κB activation and IL-8 secretion in THP-1 cells harboring a stable NF-κB reporter plasmid.

Both species of formaldehyde-treated bacteria were able to effectively induce the NF-κB pathway in the cell system or model used in examples 1 and 2 (i.e., Human THP-1 cells harboring a stably integrated NF-κB reporter plasmid) (see FIG. 4A).

Surprisingly, co-treatment with any of formaldehyde-treated *Klebsiella pneumoniae* or *Pseudomonas aeruginosa* and purified IgM showed a reduction in NF-κB signaling.

It is well-known in the prior art that activation of NF-κB signaling induces secretion of pro-inflammatory cytokines. IL-8 is a well-characterized NF-κB responsive pro-inflammatory cytokine in humans. Thus, IL-8 secretion was assessed in culture supernatants of the above-mentioned cell cultures to see if said IL-8 secretion was also responsive to bacteria (*Klebsiella pneumoniae* or *Pseudomonas aeruginosa*) and IgM (see FIG. 4B). The IL-8 cytokine secreted into the supernatant was measured by AlphaLISA, using the AlphaLISA IL-8 immunnoassay kit according to the manufacturer's protocol (Perkin-Elmer, Waltham, MA USA).

Similar to NF-κB activation, formaldehyde-fixed bacteria alone induced secretion of IL-8, to whereas co-treatment with said bacteria and IgM showed reduced secretion of IL-8, relative to the cultures treated only alone (see FIG. 4B).

Example 4. Analysis of the influence of IgM in the proliferation of peripheral blood mononuclear cells.

Since IgM showed clear effects on the NF-κB pro-inflammatory pathway, it was also assessed whether purified IgM had a more general effect on immune functions.

Proliferation of blood lymphocytes, particularly of T-cells stimulated by antigen, is one of the most basic pro-inflammatory immune responses.

Phorbol 12-myristate 13-acetate (PMA) and ionomycin, a very general proliferation stimulant, were used to induce proliferation of peripheral blood mononuclear cells, more precisely blood T-lymphocytes or T-cells.

Human peripheral blood mononuclear cells were cultured in RPMI with 10% heat inactivated human serum. For proliferation assays, $3\times10^5$ cells were seeded in each well of a 96-well plate using culture media.

T-cells were treated with 10 ng/mL PMA and 0.5 µM ionomycin for 3 days. In case IgM was used cells were treated or co-treated with purified IgM (at a final concentration of approximately 5 mg/mL and at least 95% purity) at the time of treatment, depending on the case.

Cell titer for the different groups was measured using Cell Titer Glow (Promega Corp. Madison, WI, USA) performed according to the manufacturer's instructions, and based on the measurement of the induction of cell proliferation as a function of ATP content.

Figure 5:
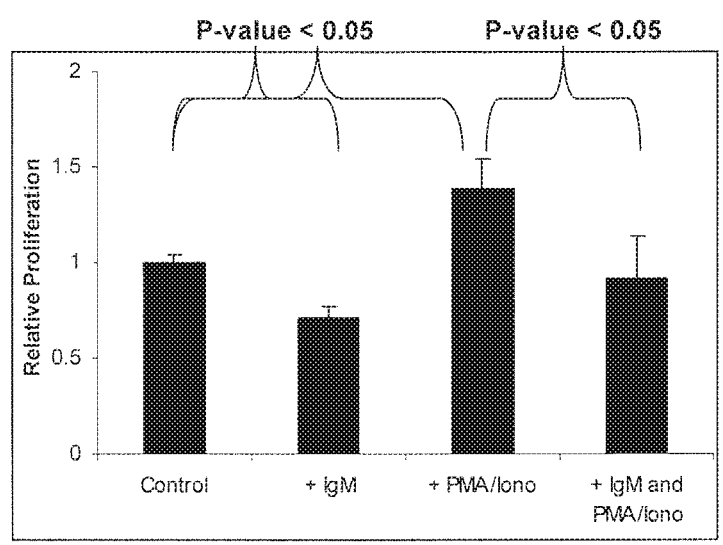
FIG. 5 shows the results obtained for the experiment regarding the IgM-mediated blockage of Phorbol 12-myristate 13-acetate (PMA)/ionomycin-induced cell proliferation 3125750 v13 in peripheral blood mononuclear cells (PBMCs), particularly T-cells. The fold increase in relative proliferation with respect to the control group is indicated on the y-axis, as measured by Cell Titer Glow, and is proportional to the induction cell proliferation. The various treatment groups are shown on the x-axis. Standard deviation is indicated on each bar.

After 3 days of PMA/ionomycin stimulation, a significant increase in proliferation was observed in peripheral blood mononuclear cells (see FIG. 5). Treatment of cells with IgM, in either the presence or absence of PMA/ionomycin, reduced the proliferation of peripheral blood mononuclear cells relative to control untreated cells and relative to PMA/ionomycin treatment. This observance was highly surprising since PMA/ionomycin is a very powerful, very non-specific mitogen. This implies that IgM has modulatory effects on the immune response itself.

What is claimed is:

1. A composition comprising at least 5 mg/mL isolated IgM and a pharmaceutically acceptable carrier, wherein the composition has at least 95% (w/v) of IgM purity and wherein IgG has been removed, wherein the pharmaceutically acceptable carrier is petroleum, peanut oil, soybean oil, mineral oil, sesame oil, polyethylene glycol, glycerin, propylene glycol, aqueous dextrose, a glycerol solution, or an excipient, wherein the excipient is selected from the group consisting of starch, gelatin, silica gel, sodium stearate, glycerol monostearate, talc, glycerol, propylene glycol, a wetting or emulsify agent, or a combination thereof.

2. The composition according to claim 1, characterized in that IgM is recombinant.

3. The composition according to claim 1, characterized in that IgM is plasma-derived.

4. The composition according to claim 1, characterized in that IgM is cell culture-derived.

5. The composition according to claim 1, characterized in that IgM is transgenic.

6. The composition according to claim 1, characterized in that IgM is chemically synthesized.

7. The composition according to claim 3, wherein IgM is plasma-derived IgM and is isolated from a suitable fraction of plasma.

8. The composition according to claim 1, characterized in that the composition further comprises one or more anti-inflammatory molecules, small molecule antibiotics, molecules that are antimicrobial in nature, natural or synthetic peptide antimicrobials, proteins with antimicrobial properties, other immunomodulators or combinations thereof.

9. The composition according to claim 8, wherein the composition further comprises vancomycin, meropenem, lactoferrin or combinations thereof.

10. The composition according to claim 1, wherein IgM is enriched against an exotoxin, secreted protein, microbial species, or combination thereof.

11. The composition according to claim 1, wherein the pharmaceutically acceptable carrier is synthetic.

12. The composition according to claim 1, wherein the pharmaceutically acceptable carrier is a diluent, an excipient, an adjuvant, or a vehicle.

13. The composition according to claim 1, wherein the wetting or emulsifying agent is selected from the group consisting of benzyl alcohol, methyl parabens, sodium bisulfite, ethylenediaminetetraacetic acid, or dextrose.

14. The composition of according to claim 1, wherein the composition further comprises vancomycin, meropenem, or a combination thereof.

* * * * *